United States Patent
Radcliffe

[19]

[11] Patent Number: 5,948,021
[45] Date of Patent: Sep. 7, 1999

[54] HYDRAULIC CYLINDERS FOR LIMB GAIT CONTROL

[75] Inventor: Charles W. Radcliffe, Lafayette, Calif.

[73] Assignee: Hosmer-Dorrance Corporation, Campbell, Calif.

[21] Appl. No.: 09/028,720

[22] Filed: Feb. 24, 1998

[51] Int. Cl.⁶ ........................................................ A61F 2/64
[52] U.S. Cl. .......................... 623/44; 623/39; 188/287; 188/285; 188/322.19
[58] Field of Search .................. 623/44, 43, 46, 623/39, 26; 188/287, 315, 285, 313, 322.19

[56] References Cited

U.S. PATENT DOCUMENTS

| | | | |
|---|---|---|---|
| 4,044,865 | 8/1977 | Tourunen | 188/287 |
| 4,056,040 | 11/1977 | Fussangel | 188/287 X |
| 4,212,087 | 7/1980 | Mortenson | 623/26 |
| 4,595,179 | 6/1986 | Glabiszewski | 267/8 R |
| 5,376,135 | 12/1994 | Aulie | 623/43 |
| 5,405,409 | 4/1995 | Knoth | 623/44 |
| 5,443,521 | 8/1995 | Knotch et al. | 623/44 |

FOREIGN PATENT DOCUMENTS

| | | | |
|---|---|---|---|
| 940 033 | 3/1956 | Germany | 188/313 |
| 1284878 | 8/1972 | United Kingdom | 623/39 |

*Primary Examiner*—David H. Willse
*Attorney, Agent, or Firm*—Thomas Schneck; John P. McGuire, Jr.

[57] ABSTRACT

A hydraulic cylinder control unit for gait control of a prosthetic limb which features two cylindrical tubes that are eccentric with respect to each other. The inner tube houses hydraulic fluid and the gap between the two tubes serves as a displacement chamber as a piston, mounted on a piston rod, moves through the fluid in the inner tube. When the outer tube is rotated about the inner tube, the gap between the tubes changes which either increases or decreases the flow allowed between the tubes. This changes the resistance which controls the rate of swing of an artificial limb. The resistance is easily adjustable by a simple rotation of the outer cylindrical tube. A floating sealed piston is additionally provided at the bottom of the inner tube. The sealed piston moves upwards or downwards depending on the balance of forces between the fluid force above the piston and the stored energy force below the sealed piston. The stored energy force can be either a spring or compressed gas and helps to return stored energy to the system and reduces the amount of energy required by the person in walking.

21 Claims, 4 Drawing Sheets

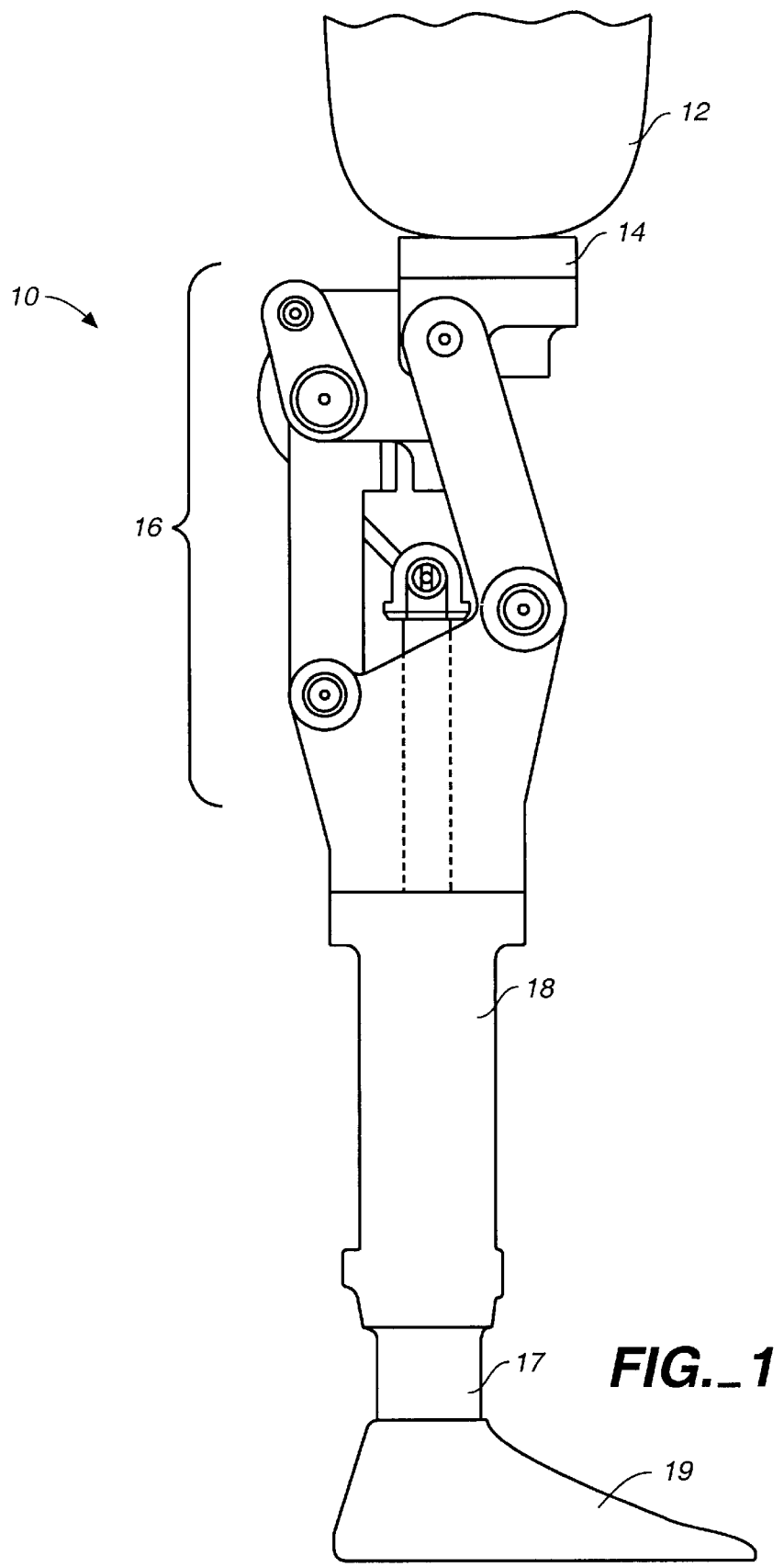
FIG._1

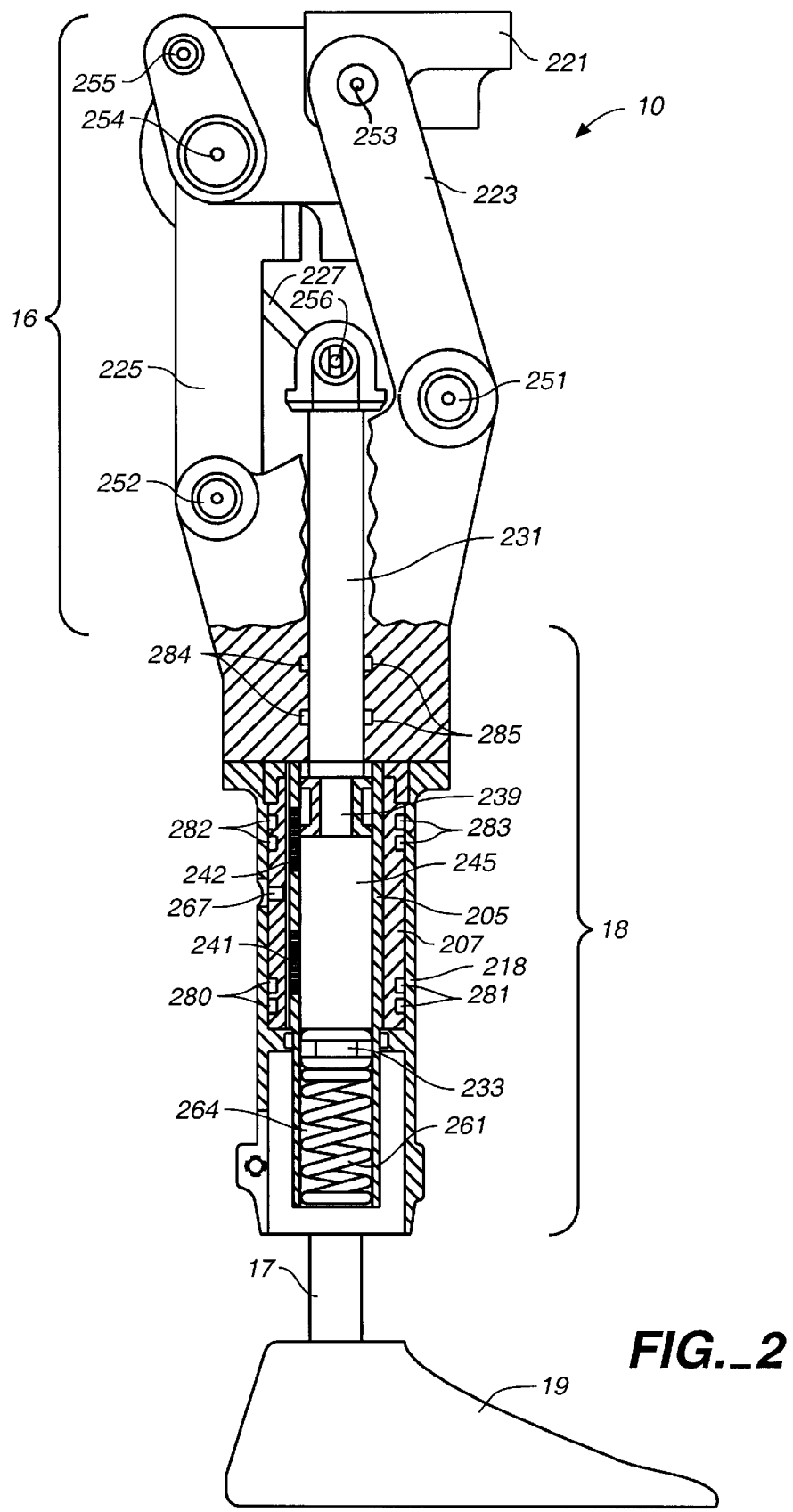
FIG._2

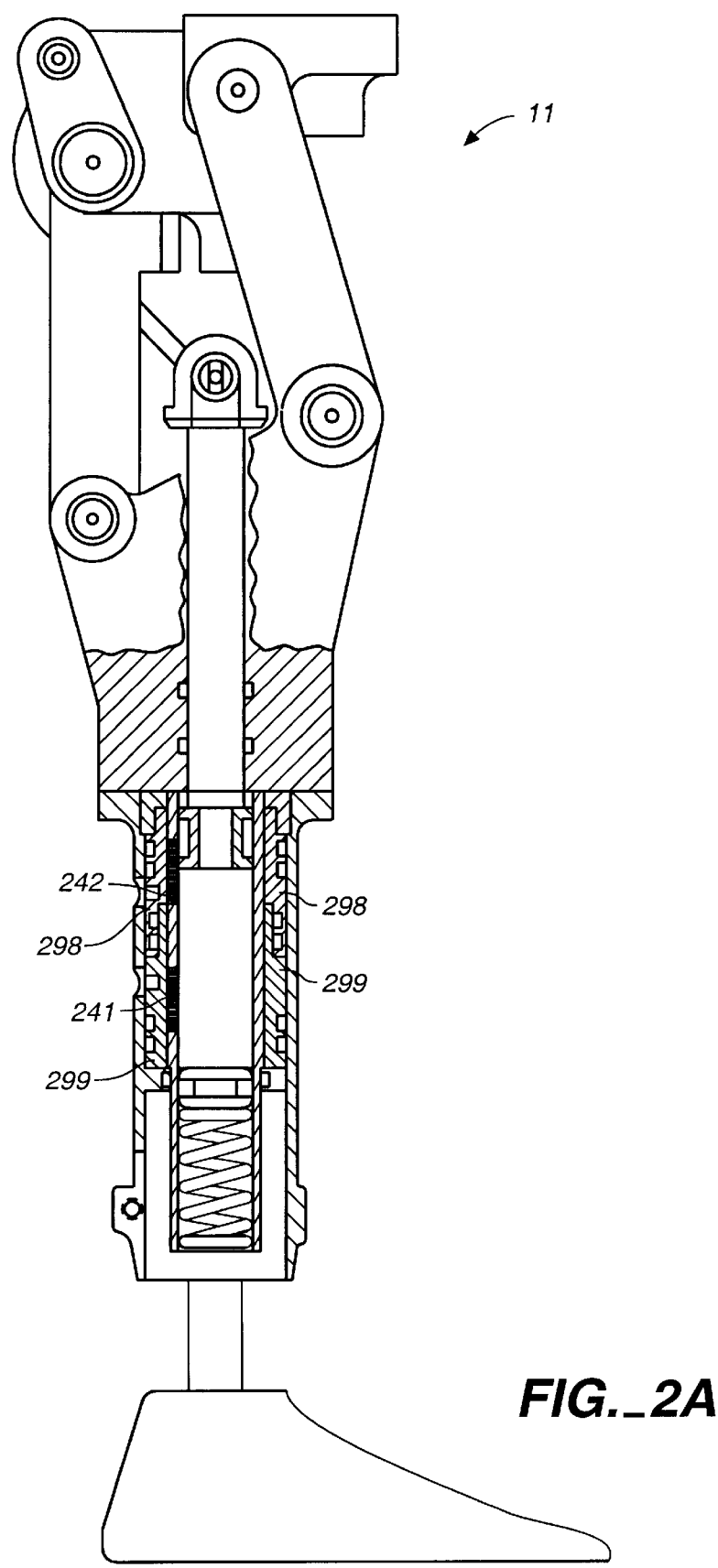
FIG._2A

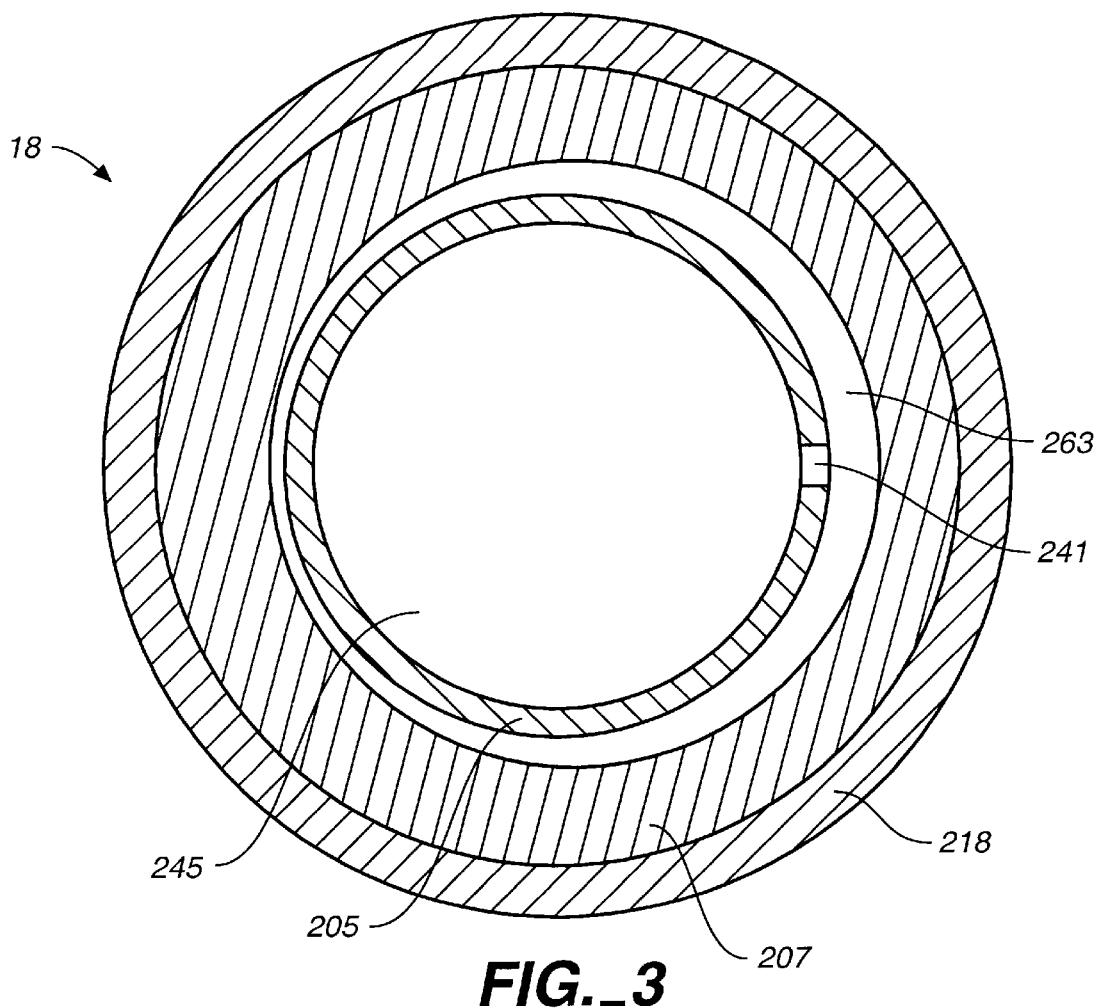
FIG._3

HYDRAULIC CYLINDERS FOR LIMB GAIT CONTROL

FIELD OF THE INVENTION

The present invention relates to hydraulic damping devices, particularly for use in controlling the gait of a prosthetic leg.

BACKGROUND ART

Human locomotion studies made at the University of California, Berkeley, in 1950, provided the basic data for theoretical calculations of mechanisms which would be used in an above-knee prosthesis to approximate the walking gait of a normal person. The prior art mechanical friction knee mechanisms were shown to have a fundamental deficiency in that the devices provided the same amount of frictional resistance to movement at slow cadences as to movement at fast cadences. As a result, adjustment for absorbing the desired energy during swing phase was only optimum at one cadence. At faster cadences, braking was insufficient, resulting in excessive heel rise and hyperflexion. At slow cadences, the braking resulted in inadequate flexion and extension. It was found that the use of hydraulic damping in the knee mechanism could be used to achieve nearly normal leg action over a wide cadence range. This is due to the characteristics of hydraulic flow through ports or orifices in which the resistance to flow increases with increasing cadence at a rate almost exactly balancing the energy absorbing requirements of the prosthesis. This permits a design that provides for the correct heel rise and extension in swing phase, independent of cadence.

In hydraulic damping devices, the device usually includes a hydraulic cylinder and piston unit defining an annular chamber between the inner wall of the cylinder and the piston for storing a hydraulic medium. The piston is provided with an annular shoulder which divides the storing chamber into two partial chambers, each being connected via damping passages so that the hydraulic medium may pass from one partial chamber into the other, and vice versa. Usually, the partial chambers are arranged in axial relation to one another.

Also known in the prior art is to provide two cylinder spaces of variable volume, whereby the piston, during its movement, reduces the volume of the first partial chamber and the hydraulic fluid flows through connecting conduits into the correspondingly enlarged second partial chamber. For example, during the flexion cycle of the leg movement, the piston would move downward and the fluid flows through the connecting conduits to the upper chamber. As the piston moves downward, the connecting conduits are covered by the piston, causing pressure to build up below the piston and causing programmed deceleration of the prosthesis. A series of adjustable valves are used to control the peak value of the deceleration and the amount of energy absorbed in limiting heel rise. Thus, by adjusting the valves, the amount of resistance in the prosthetic leg can be increased or decreased. The same action occurs during the leg extension cycle as well, except that in the leg extension cycle, the piston usually moves upward through the cylinder. As the piston moves upwards, the connecting conduits are covered and pressure builds above the piston to cause programmed deceleration of the prosthesis in a natural manner. Again, a series of adjustable valves are used to control peak deceleration and, thus, the amount of energy absorbed in stopping extension travel.

The main disadvantages of the prior art valve system hydraulic control units is that some are rather large and bulky, so that they require a relatively large installation space; and most are difficult to manufacture, since they require many parts.

Other prior art hydraulic control units include U.S. Pat. Nos. 5,405,409 and 5,443,521 to Knoth, U.S. Pat. No. 4,595,179 to Glabiszewski, and U.S. Pat. No. 5,376,135 to Aulie. The Knoth patents disclose a hydraulic control device which uses fluid control ports, channels and adjustable gaps defined by an axially adjustable sleeve and a control bushing for damping the movement of the piston rod. The piston rod encloses a preferably sealed gas pressurized flexible bladder which forms an oil accumulator during inward movement of the piston rod into a displacement chamber and also produces variable forces for moving the piston rod outwardly to its extended position. The Glabiszewski patent discloses a hydraulic damping unit for use in artificial joints where a hollow throttling piston is guided in a main piston and is formed with an annular recess which communicates with respective variable volume chambers via passages passing through the jacket of the main piston at both sides of the pistons shoulder. In the range of both passages, the bottom of the recess of the throttling piston is connected to the outer surfaces of the latter via a sloping annular surface which depending on the relative position of the throttling piston to the main piston, adjusts the clearance of the passages to control the resistance to flow of the hydraulic liquid. The Aulie patent discloses an adjustable hydraulic damper involving a piston member within a hydraulic cylinder where the hydraulic cylinder wall is adjustably deformed to vary the annular space between a piston head and the inside cylinder wall through which hydraulic fluid must pass. The wall of the cylinder is adjustably deformed through an annular ramp formed circumferentially about the outside of the cylinder and having an angled bearing surface.

SUMMARY OF THE INVENTION

It is an object of the present invention to provide a hydraulic control unit for gait control of a prosthetic limb that can be adjusted conveniently and that is smaller and easier to manufacture.

This object is achieved in the present invention which is a hydraulic cylinder unit which features two cylindrical tubes that are eccentric with respect to each other. When the outer tube is rotated about the inner tube, the gap between the tubes changes, which either increases or decreases the flow allowed between the tubes. This changes the resistance which controls the rate of swing of an artificial limb. The inner tube has inlet and outlet ports on one side of the tube. When the gap between the outer tube and the inner tube on the side with the ports is larger, there is less resistance, and when the gap is smaller, there is more resistance. The resistance can be adjusted by a simple rotation of the outer cylinder, which can be accomplished by the person who uses the artificial limbs by a simple key turn. Thus, since there are no valves to adjust, it is easy for the user to make minor adjustments to the resistance of the leg. Additionally, because there are no valves, the unit has less parts so it is easier to manufacture and it is smaller and more convenient to install.

BRIEF DESCRIPTION OF THE DRAWINGS

FIG. 1 is a side view of a prosthetic leg assembly.

FIG. 2 is a side view of a prosthetic leg assembly with a portion broken away to show the assembly of a hydraulic control unit constructed in accordance with the present invention.

FIG. 2A is a side view of a prosthetic leg assembly with a portion broken away to show the assembly of an alternate embodiment of the hydraulic control unit shown in FIG. 2.

FIG. 3 is a top cross section view of a hydraulic control unit assembly.

BEST MODE FOR CARRYING OUT THE INVENTION

FIG. 1 illustrates a prosthetic or artificial leg 10 which includes a bracket 14 secured to a cup shaped socket portion 12 adapted to receive the residual portion of an amputee's leg. The prosthetic leg 10 also includes a foot portion 19 which serves to make contact with the ground and is connected to a hollow lower leg portion 17 which is connected to the hydraulic control unit 18. The hydraulic control unit 18 is connected to the socket portion 12 and bracket 14 through a four-bar linkage system 16 which forms a knee joint. FIG. 2 shows a more detailed view of the prosthetic leg 10. Referring first to the upper portion of FIG. 2, the four-bar linkage system 16 consists of a socket base 221 (which connects to the bracket 14 and socket 12 shown in FIG. 1), and an anterior link 223 connected to socket base 221 and pivotally rotational through bearings 253 and 251. The four-bar linkage system also includes a posterior link 225, which is connected to socket base 221 through bearing 254 and is pivotal around bearing 252, and a piston link 227, which is connected to the base through bearing 255 and is connected to a piston rod 231 through bearing 256. The anterior link 223 and the posterior link 225 connect to the upper portion of the hydraulic control unit 18, while the piston rod 231 extends into the hydraulic control unit 18. Alternatively, the four-bar linkage system 16, could be replaced by an endoskeletal frame with a single axis of rotation for the knee, otherwise known as a single axis knee.

Referring to the lower portion of FIG. 2, the hydraulic control unit 18 has an metal outer housing 218 that surrounds the inner portions of the unit. Within the housing 218 are two cylinders, the control cylinder 207 and the inner cylinder 205, which are made of anodized aluminum and are eccentric with respect to one another. Other types of material may be used for the cylinders, but aluminum was chosen for the preferred embodiment of this invention due to its strength, its being lightweight and its ability to be compatible with anodized surface finishes. Additionally, it is preferred that the two cylinders be made out of the same material, as having different materials could lead to differential thermal expansion, which could cause an unwanted change in the distance between the two cylinders. The inner cylinder 205, defines an oil reservoir 245 that is filled with hydraulic fluid. The piston rod 231 carries a cylindrical piston 239 through the oil reservoir 245 within the inner cylinder 205.

The control cylinder 207 is eccentric to the inner cylinder 205 by approximately 0.010 inches. This is illustrated in FIG. 3 which shows a top view of a cross section of the hydraulic control unit 18. As shown, the outer housing 218 encloses the control cylinder 207 and the inner cylinder 205, which encompasses the oil reservoir 245. Between the control cylinder 207 and the inner cylinder 205, there is a gap 263, which is larger on one side than on the other side. In FIG. 3, a typical outlet (or inlet) hole 241 of inner cylinder 205 is shown to be on the side having the larger gap area. When the large portion of the gap 263 is on the side of the outlet hole, there is more fluid flow and, therefore, less resistance, conversely, the control cylinder is rotated such that if the outlet hole is on the side where there is the smaller portion of gap 263, then there is less fluid flow and more resistance.

Referring to FIG. 2, the unit in operation works as follows. During the flexion cycle, when the knee begins to flex, the piston link 227 rotates clockwise around bearing 256 and the piston rod 231 moves downward. This drives the piston 239 downward through the oil reservoir 245. As the piston 239 moves downwards, the hydraulic fluid is pushed out of the oil reservoir through outlet holes 241 into the control cylinder 207. The fluid displaced by the piston rod 231 and piston 239 travels through the control cylinder 207 and re-enters the reservoir 245 through inlet holes 242 on top of the piston 239. As the piston 239 moves downwards, the pressure in the oil reservoir 245 below the piston 239 begins to increase. As the pressure builds up, the piston 239 decelerates until it comes to a stop at maximum flexion, then reverses its motion to begin extension. The rate of deceleration, as explained earlier, is based on the positioning of the eccentric control cylinder 207 in relation to the inner cylinder 205. In FIG. 2, the large portion of gap 263 is shown to be on the same side as the inlet holes 242 and outlet holes 241, so there would be less resistance and the leg would decelerate at a slower rate.

After the knee completes the flexion motion, the leg will begin the extension cycle. As the leg extends, the piston link 227 rotates in the other direction, pulling the piston rod 231 and piston 239 upward through the oil reservoir 245. As the piston 239 moves upward, the fluid is pushed out of the oil reservoir 245 through holes 242. The fluid travels up through the control cylinder 207 and enters below the piston 239 at holes 241. As the pressure above the piston 239 begins to increase, the piston 239 decelerates, as previously explained, so that the leg stops in full extension with a normal motion. At the bottom of the oil reservoir 245 is a floating sealed piston 233. The sealed piston 233 separates the oil reservoir 245 from the bottom part of the inner cylinder 205, the bottom part of the inner cylinder 205 being called the accumulator 264. Beneath the sealed piston 233, there is an energy storage spring 261, which aids extension by extending and returning stored energy to the system. This spring 261 helps to achieve normal gait patterns and also reduces the energy required by the person in walking. Alternatively, the spring 261 could be replaced by compressed gas in the accumulator 264. The compressed gas would serve the same function as the spring 261 in aiding to return the stored energy to the system. In order to prevent the fluid from leaking through the cylinders to the outside, a series of O-rings, such as 280, 281, 282, 283, 284, and 285 are provided throughout the unit.

Additionally provided is a resistance indicator 267 on the side of the unit in order to indicate the setting of the resistance and positioning between the inner cylinder 205 and the control cylinder 207. The resistance indicator 267 consists of a series of cylindrical holes on the control cylinder 207, labelled to indicate the position of the cylinders. (For example, the cylindrical holes could be labelled "1" through "9", with "1" being the position where there is the maximum size gap in front of the inlet holes and "9" being the position where there is the minimum size gap.) The resistance of the leg can be adjusted by changing the orientation of the control cylinder 207 and the inner cylinder 205. This is accomplished rotating the control cylinder 207 by using a tool, such as a key or wrench, to rotate the cylindrical holes. The cylindrical hole that is shown on the resistance indicator 267 indicates the present position of the control cylinder 207. In this way, it is convenient to adjust the resistance of the prosthetic device to suit the specific requirements of the user.

In another embodiment 11 of the present invention, shown in FIG. 2A, the control cylinder made of two pieces, with one piece 298 covering the inlet holes 242 and the other piece 299 covering the outlet holes 241. This construction would allow for independent adjustment of the inlet and outlet holes during the flexion and extension cycles.

I claim:

1. A hydraulic control unit for use with a prosthetic leg assembly of the type having a load-bearing linkage system or a single axis-knee assembly for providing flexion and extension of a leg, the hydraulic control unit comprising:

a pair of cylinders aligned in eccentric relation to each other, one of the pair of cylinders being a fluid confining control cylinder and a second of the pair of cylinders being an inner cylinder, the inner cylinder being within the control cylinder and defining a fluid reservoir therein, with a gap being a spacing between the control cylinder and the inner cylinder, the gap defining a fluid displacement chamber and having a size that is larger on one side of the inner cylinder than on an opposite side;

a series of openings in the inner cylinder for passing fluid between the fluid reservoir and the fluid displacement chamber with the size of the gap adjacent to the openings being adjustable by a rotational position of the control cylinder;

a piston assembly having a rod with an inner portion extending into the inner cylinder, an outer portion projecting from the inner cylinder, and a first piston located on the inner portion of the piston rod within the fluid reservoir;

a supply of hydraulic fluid within each of the fluid reservoir and the fluid displacement chamber, the fluid flowing through said series of openings in response to axial movement of the piston and piston rod within the fluid reservoir to effect damping of the piston rod; and means for adjusting the rotational position between the control cylinder and the inner cylinder.

2. A hydraulic control unit for use with a prosthetic leg assembly as in claim 1, further comprising:

a floating sealed movable second piston within the inner cylinder and defining a bottom side of the fluid reservoir, the floating sealed second piston having a stored energy force means applied on a bottom side of the second piston for returning stored energy to the piston assembly, the floating sealed piston being movable through the inner cylinder to compensate for fluid displaced by the piston rod entering or leaving the fluid reservoir as the piston assembly moves within the fluid reservoir.

3. A hydraulic control unit for use with a prosthetic leg assembly, as in claim 2, further comprising:

an accumulator chamber being located beneath the floating sealed piston, the stored energy force means being located in the accumulator chamber.

4. A hydraulic control unit for use with a prosthetic leg assembly, as in claim 3, wherein the stored energy force means is a spring.

5. A hydraulic control unit for use with a prosthetic leg assembly, as in claim 3, wherein the stored energy force means is compressed gas.

6. A hydraulic control unit for use with a prosthetic leg assembly, as in claim 1, further comprising an outer housing providing a load-bearing member for a load-bearing linkage system, the pair of cylinders being located within the outer housing.

7. A hydraulic control unit for use with a prosthetic leg assembly, as in claim 6, further comprising:

means for preventing the supply of hydraulic fluid from leaking through the outer housing.

8. A hydraulic control unit for use with a prosthetic leg assembly, of the type having a load-bearing linkage system or a single axis knee assembly for providing flexion and extension of a leg, the hydraulic control unit comprising:

an inner fixed cylinder and a rotatable fluid tight control cylinder surrounding the inner cylinder, and defining a fluid reservoir within the inner cylinder, the control cylinder having an eccentric rotational relation to the inner cylinder such that there is a gap between the inner cylinder and the control cylinder, the gap defining a fluid displacement chamber and having a size that is larger on one side of the inner cylinder than on an opposite side;

a series of openings between the inner cylinder and the control cylinder for passing fluid between the fluid reservoir of the inner cylinder and the gap defining the fluid displacement chamber;

a piston assembly having a rod with an inner portion extending into the inner cylinder and an outer portion projecting from the inner cylinder, with a first piston being located on the inner portion of the piston rod within the fluid reservoir;

a supply of hydraulic fluid within each of the fluid reservoir and the gap defining the fluid displacement chamber, the fluid flowing between said fluid reservoir and the gap defining the fluid displacement chamber in response to axial movement of the first piston and the piston rod within the fluid reservoir to effect damping the piston rod;

a floating sealed movable, second piston within the inner cylinder and defining a bottom side of the fluid reservoir, the floating sealed second piston being movable through the inner cylinder to compensate for fluid displaced by the piston rod entering or leaving the fluid reservoir as the piston assembly moves within the fluid reservoir and having a stored energy force means applied on a bottom side of the second piston for returning stored energy to the piston assembly; and means for adjusting the rotational position between the control cylinder and the inner cylinder, thereby adjusting the size of the gap on a side of the inner cylinder adjacent to the series of openings.

9. A hydraulic control unit for use with a prosthetic leg assembly, as in claim 8, wherein the stored energy force means is a spring.

10. A hydraulic control unit for use with a prosthetic leg assembly, as in claim 8, wherein the stored energy force means is compressed gas.

11. A hydraulic control unit for use with a prosthetic leg assembly, as in claim 8, wherein the means for adjusting the rotational position between the control cylinder and the inner cylinder includes a means for rotation of the control cylinder.

12. A hydraulic control unit for use with a prosthetic leg assembly, as in claim 8, wherein the first piston and the piston rod axially move through the fluid reservoir displacing fluid from the fluid reservoir to the fluid displacement chamber.

13. A hydraulic control unit for use with a prosthetic leg assembly, as in claim 8, further comprising an outer housing providing a load-bearing member for a load-bearing linkage system, the inner cylinder and control cylinder being located within the outer housing.

14. A hydraulic control unit for use with a prosthetic leg assembly, as in claim 13, further comprising:

sealant means for preventing the supply of hydraulic fluid from leaking through the outer housing.

15. A hydraulic control unit for use with a prosthetic leg assembly, as in claim 13, herein the inner cylinder, the control cylinder and the outer housing are made of anodized aluminum.

16. A hydraulic control unit for use with a prosthetic leg assembly of the type having a load-bearing linkage system or a single axis knee assembly for providing flexion and extension of a leg, the hydraulic control unit comprising:

- a pair of cylinders aligned in eccentric relation to each other, one of the pair of cylinders being a fluid confining control cylinder and a second of the pair of cylinders being an inner cylinder, the inner cylinder being within the control cylinder and defining a circumference of a fluid reservoir with a gap being the spacing between the inner cylinder and the control cylinder, the gap defining a fluid displacement chamber and having a size that is larger on one side of the inner cylinder than on an opposite side;
- a number of extension resistance and flexion resistance holes on a side of the inner cylinder for passing fluid between the fluid reservoir of the inner cylinder and the fluid displacement chamber;
- a piston assembly having a rod with an inner portion extending into the inner cylinder and an outer portion projecting from the inner cylinder with a first piston being located on the inner portion of the piston rod within the fluid reservoir, wherein the first piston and piston rod may axially move through the fluid reservoir;
- a supply of hydraulic fluid within each of the fluid reservoir and the gap defining the fluid displacement chamber, the fluid flowing through said extension resistance holes and said flexion resistance holes in response to the axial movement of the first piston and the piston rod within the fluid reservoir to effect damping of the piston rod;
- a floating sealed, movable second piston, within the inner cylinder and defining a bottom side of the fluid reservoir, the floating sealed second piston having a stored energy force means applied on a bottom side of the second piston for returning stored energy to the piston assembly, the floating sealed piston being movable through the inner cylinder to compensate for fluid displaced by the piston rod entering or leaving the fluid reservoir as the piston assembly moves within the fluid reservoir; and
- an accumulation chamber being located within the inner cylinder, beneath the floating sealed piston;
- means for adjusting a rotational position between the control cylinder and the inner cylinder thereby adjusting the size of the gap which defines the fluid displacement chamber on a side of the inner cylinder adjacent to the extension resistance and flexion resistance holes.

17. A hydraulic control unit for use with a prosthetic leg assembly, as in claim 16, wherein the stored energy force means is a spring.

18. A hydraulic control unit for use with a prosthetic leg assembly, as in claim 16, wherein the stored energy force means is compressed gas.

19. A hydraulic control unit for use with a prosthetic leg assembly, as in claim 16, wherein the control cylinder is made of two pieces, with one of said pieces covering the extension resistance holes and the other of said pieces covering the flexion resistance holes.

20. A hydraulic control unit for use with a prosthetic leg assembly, as in claim 16, further comprising an outer housing providing a load-bearing member for a load-bearing linkage system, the pair of cylinders being located within the outer housing.

21. A hydraulic control unit for use with a prosthetic leg assembly, as in claim 20, further comprising:

- means for preventing the supply of hydraulic fluid from leaking through the outer housing.

* * * * *